United States Patent
Shroff et al.

(10) Patent No.: US 9,219,866 B2
(45) Date of Patent: Dec. 22, 2015

(54) DYNAMIC ADJUSTMENT OF MULTIMODE LIGHTFIELD IMAGING SYSTEM USING EXPOSURE CONDITION AND FILTER POSITION

(71) Applicants: Sapna A. Shroff, Menlo Park, CA (US); Kathrin Berkner, Los Altos, CA (US)

(72) Inventors: Sapna A. Shroff, Menlo Park, CA (US); Kathrin Berkner, Los Altos, CA (US)

(73) Assignee: Ricoh Co., Ltd., Tokyo (JP)

( * ) Notice: Subject to any disclaimer, the term of this patent is extended or adjusted under 35 U.S.C. 154(b) by 0 days.

(21) Appl. No.: 13/735,297

(22) Filed: Jan. 7, 2013

(65) Prior Publication Data

US 2014/0192255 A1   Jul. 10, 2014

(51) Int. Cl.
| | |
|---|---|
| H04N 5/235 | (2006.01) |
| H04N 5/225 | (2006.01) |
| G01N 21/27 | (2006.01) |
| G01J 3/28 | (2006.01) |
| G01J 3/36 | (2006.01) |
| G01J 3/02 | (2006.01) |
| G01J 3/32 | (2006.01) |
| H04N 5/33 | (2006.01) |
| G01J 3/12 | (2006.01) |
| G01N 21/17 | (2006.01) |

(52) U.S. Cl.
CPC ............ *H04N 5/2353* (2013.01); *G01J 3/0208* (2013.01); *G01J 3/2803* (2013.01); *G01J 3/32* (2013.01); *G01J 3/36* (2013.01); *G01N 21/27* (2013.01); *H04N 5/2254* (2013.01); *G01J 2003/1213* (2013.01); *G01J 2003/1221* (2013.01); *G01J 2003/1243* (2013.01); *G01N 2021/1797* (2013.01); *H04N 5/332* (2013.01)

(58) Field of Classification Search
USPC .................................................. 348/270, 271
See application file for complete search history.

(56) References Cited

U.S. PATENT DOCUMENTS

| | | | |
|---|---|---|---|
| 5,227,890 A | 7/1993 | Dowski, Jr. | |
| 5,521,695 A | 5/1996 | Cathey, Jr. et al. | |
| 5,748,371 A | 5/1998 | Cathey, Jr. et al. | |
| 5,870,179 A | 2/1999 | Cathey, Jr. et al. | |
| 5,926,283 A | 7/1999 | Hopkins | |
| 5,982,497 A | 11/1999 | Hopkins | |
| 6,021,005 A | 2/2000 | Cathey, Jr. et al. | |
| 6,069,738 A | 5/2000 | Cathey, Jr. et al. | |
| 6,313,960 B2 | 11/2001 | Marquiss et al. | |
| 6,525,302 B2 | 2/2003 | Dowski, Jr. et al. | |
| 6,842,297 B2 | 1/2005 | Dowski, Jr. | |
| 6,873,733 B2 | 3/2005 | Dowski, Jr. | |
| 6,911,638 B2 | 6/2005 | Dowski, Jr. et al. | |
| 6,927,836 B2 | 8/2005 | Nishinaga | |
| 6,940,649 B2 | 9/2005 | Dowski, Jr. | |
| 7,433,042 B1 | 10/2008 | Cavanaugh et al. | |

(Continued)

OTHER PUBLICATIONS

Cavanaugh, D.B. et al., "VNIR Hypersensor Camera System," Proc. SPIE, conference Aug. 3, 2009, online publication Aug. 17, 2009, 17 pages, vol. 7457.

(Continued)

*Primary Examiner* — Albert Cutler
(74) *Attorney, Agent, or Firm* — Fenwick & West LLP (57) ABSTRACT

An adjustable multimode lightfield imaging system. A non-homogeneous filter module is positioned at the pupil plane of the lightfield imaging system and provides the multimode capability. The filter module can be moved relative to the imaging system with the exposure conditions adjusted accordingly, thus allowing adjustment of the multimode capability.

20 Claims, 10 Drawing Sheets

(56) References Cited

U.S. PATENT DOCUMENTS

| | | |
|---|---|---|
| 7,616,841 B2 | 11/2009 | Robinson et al. |
| 7,616,842 B2 | 11/2009 | Robinson |
| 7,663,690 B2 | 2/2010 | Kurosawa |
| 7,692,709 B2 | 4/2010 | Robinson et al. |
| 7,714,982 B2 * | 5/2010 | Nagasaka ................ 355/53 |
| 8,143,565 B2 * | 3/2012 | Berkner et al. ............ 250/208.1 |
| 8,248,511 B2 | 8/2012 | Robinson et al. |
| 8,259,200 B2 * | 9/2012 | Iwasa ............................ 348/270 |
| 8,345,144 B1 * | 1/2013 | Georgiev et al. ............. 348/340 |
| 8,471,920 B2 * | 6/2013 | Georgiev et al. ........... 348/221.1 |
| 8,761,534 B2 | 6/2014 | Shroff et al. |
| 8,949,078 B2 | 2/2015 | Berkner et al. |
| 2001/0021074 A1 | 9/2001 | Marquiss et al. |
| 2002/0118457 A1 | 8/2002 | Dowski, Jr. |
| 2002/0195548 A1 | 12/2002 | Dowski, Jr. et al. |
| 2003/0057353 A1 | 3/2003 | Dowski, Jr. et al. |
| 2003/0169944 A1 | 9/2003 | Dowski, Jr. et al. |
| 2003/0173502 A1 | 9/2003 | Dowski, Jr. et al. |
| 2004/0145808 A1 | 7/2004 | Cathey, Jr. et al. |
| 2004/0190762 A1 | 9/2004 | Dowski, Jr. et al. |
| 2004/0228005 A1 | 11/2004 | Dowski |
| 2004/0257543 A1 | 12/2004 | Dowski, Jr. et al. |
| 2005/0088745 A1 | 4/2005 | Cathey, Jr. et al. |
| 2005/0197809 A1 | 9/2005 | Dowski, Jr. et al. |
| 2005/0264886 A1 | 12/2005 | Dowski |
| 2006/0077284 A1 | 4/2006 | Kurosawa |
| 2006/0187311 A1 | 8/2006 | Labaziewicz et al. |
| 2007/0025722 A1 * | 2/2007 | Matsugu et al. ............. 396/263 |
| 2007/0081224 A1 | 4/2007 | Robinson et al. |
| 2008/0204744 A1 | 8/2008 | Mir et al. |
| 2008/0266655 A1 | 10/2008 | Levoy et al. |
| 2009/0096914 A1 | 4/2009 | Domenicali |
| 2009/0135282 A1 | 5/2009 | Gidon |
| 2010/0165178 A1 * | 7/2010 | Chou et al. ................... 348/371 |
| 2010/0253941 A1 | 10/2010 | Brady et al. |
| 2011/0073752 A1 * | 3/2011 | Berkner et al. ............ 250/227.2 |
| 2012/0182438 A1 | 7/2012 | Berkner et al. |
| 2013/0027581 A1 * | 1/2013 | Price et al. ................. 348/229.1 |
| 2013/0215236 A1 | 8/2013 | Shroff et al. |

OTHER PUBLICATIONS

Choi, J. et al., "Zoom Lens Design for a Novel Imaging Spectrometer That Controls Spatial and Spectral Resolution Individually," Applied Optics, 2006, pp. 3430-3441, vol. 45.

Elliott, K.H., "A Novel Zoom-Lens Spectrograph for a Small Astronomical Telescope," Mon. Not. R. Astron. Soc., 1996, pp. 158-162, vol. 281.

Fife, K. et al., "A 3D Multi-Aperture Image Sensor Architecture," Proc. of IEEE Custom Integrated Circuits Conference, 2006, pp. 281-284.

Gehm, M. et al., "Single-Shot Compressive Spectral Imaging with a Dual-Disperser Architecture," Optics Express, Oct. 17, 2007, pp. 14013-14027, vol. 15, No. 21.

Harvey, a.R. et al., "Spectral Imaging in a Snapshot," Proc. of SPIE, 2005, pp. 110-119, vol. 5694.

Harvey, a.R. et al., "Technology Options for Hyperspectral Imaging," Proc. of SPIE, 2000, pp. 13-24, vol. 4132.

Horstmeyer, R. et al., "Flexible Multimodal Camera Using a Light Field Architecture," IEEE Conf. on Computational Photography, 2009, pp. 1-8.

Shogenji, R. et al., "Multispectral Imaging Using Compound Optics," Optics Express, Apr. 19, 2004, pp. 1643-1655, vol. 12, No. 8.

Cathey, W. Thomas et al., "New Paradigm for Imaging Systems," Applied Optics, Oct. 10, 2002, pp. 6080-6092, vol. 41.

European Extended Search Report, European Application No. 12157955.1, Mar. 14, 2013, 7 pages.

Fife, K. et al., "A Multi-Aperture Image Sensor with 0.7 μm Pixels in 0.11 μm CMOS Technology," IEEE Journal of Solid-State Circuits, Dec. 2008, pp. 2990-3005, vol. 43, No. 12.

Maeda, P. Y. et al., "Integrating Lens Design with Digital Camera Simulation," 5678 SPIE Proceedings SPIE Electronic Imaging, Feb. 2005, pp. 48-58, San Jose, CA.

Chinese First Office Action, Chinese Application No. 201410003320.2, Sep. 1, 2015, 21 pages.

* cited by examiner

DYNAMIC ADJUSTMENT OF MULTIMODE LIGHTFIELD IMAGING SYSTEM USING EXPOSURE CONDITION AND FILTER POSITION

BACKGROUND OF THE INVENTION

1. Field of the Invention

This invention relates generally to multimode imaging systems using filter modules, such as plenoptic imaging systems using filter modules.

2. Description of the Related Art

A multimode imaging system is an imaging system that can capture information beyond the usual spatial information acquired by conventional imaging systems (e.g., those based on RGB Bayer patterns). For example, a multimode imaging system might acquire additional spectral information (multispectral and hyperspectral systems) to be used for spectral analysis or identification of substances. Multimode imaging systems might also capture information about the polarization of a scene, or even provide a higher dynamic range than that provided by the inherent capability of the detector array.

Acquiring this additional information can be difficult since most commercially available detector arrays spatially segment the incoming image into a two-dimensional image signal. Traditionally, the additional information of spectra, polarization or other modes was acquired by time multiplexing. For example, in spectral imaging applications, it might be desirable to acquire radiation from an object at different wavelengths of interest. The number of wavelength bands of interest may be between 5 and 20 for multispectral imagers and more than 20 for hyperspectral imagers. Traditional multispectral or hyperspectral imagers are based either on a filter wheel that contains wavelength filters that correspond to the wavelength bands of interest or on dispersive elements such as prisms or gratings. In case a filter wheel is used, at any one time, only one of the wavelength filters is positioned in the imaging path. The filter wheel rotates in order to switch from one wavelength filter to the next. Thus, the multispectral or hyperspectral imaging is implemented in a time multiplexed manner. However, the resulting systems can be large and complicated. In case dispersive elements are used to spatially separate different wavelengths, the light is typically dispersed along one dimension of the detector array. The other dimension is used to capture one spatial dimension of the object. However, it is difficult to also capture the second spatial dimension of the object. Sometimes, time multiplexing is introduced to capture the second spatial dimension, for example by scanning.

Recently, there has been an increased attention on acquiring multimode information of a scene simultaneously, or in a "single snapshot." These single-snapshot systems multiplex the different mode signals onto different detector pixels in the detector array. That is, the multimode information is spatially multiplexed rather than time multiplexed.

Single snapshot multispectral imaging architectures can generally be categorized into two classes. One class uses dispersive elements, such as prisms or gratings, to spatially separate different wavelengths in combination with some beam splitting element, e.g. a prism or a mask. This architecture has the disadvantage that the dispersive element is typically applied to either a collimated beam or at an intermediate image plane. As a result, many of these systems can be quite large and/or have a limited field of view.

In the other class of single snapshot imagers, separate filters are attached to each detector in a manner similar to the RGB Bayer pattern found in conventional color imaging systems. That is, a color filter array is laid out on top of the detector array, so that individual filters (which will be referred to as micro-filters) each filter the light directed to individual detectors. The individual micro-filters are designed to implement the multimode imaging. For example, the filter array might include micro-filters with 20 different wavelength responses in order to implement multispectral imaging. One disadvantage of this class of systems is the increased cost and complexity of manufacturing. Because there is a one-to-one correspondence between micro-filters and detectors, and because the micro-filters are attached to the detectors, the micro-filters are the same size as the detectors, which is small. The many different small micro-filters must then be arranged into an array and aligned with the underlying detectors. Another disadvantage is the lack of flexibility. Once the micro-filter array is attached to the detector array, it is difficult to change the micro-filter array.

Thus, there is a need for improved multimode imaging systems.

SUMMARY OF THE INVENTION

The present invention overcomes the limitations of the prior art by providing an adjustable multimode lightfield imaging system. A non-homogeneous filter module, for example a filter array, is positioned at or near the pupil plane of the main (or primary) image-forming optical module of the lightfield imaging system and provides the multimode capability. The filter module can be moved relative to the imaging system with the exposure conditions adjusted accordingly, thus allowing adjustment of the multimode capability.

In one embodiment, an adjustable multimode lightfield imaging system includes an optical module that forms an optical image of an object. The optical module is characterized by imaging optics, a pupil plane and an image plane. A filter array is positioned approximately at the pupil plane. The filter array is moveable relative to the optical module. An array of micro-imaging elements is positioned approximately at the image plane. A detector array is positioned such that the micro-imaging elements image the filter array onto the detector array. The detector array captures a multimode image of the object according to an exposure condition. Changing the position of the filter array changes the multimode capability of the imaging system. A controller adjusts the exposure condition in response to the position of the filter array.

The exposure condition can be adjusted in different ways. For example, the controller could adjust the strength of a light source illuminating the object, as might be the case in a microscope setting. Alternately, the controller could adjust a light throughput of the imaging system, for example by adjusting the attenuation of a neutral density filter in the system. The controller could also adjust the exposure/integration time of the detector array.

In another aspect, the exposure condition is adjusted in response to an image quality metric. Examples of such metrics include signal to noise ratio (SNR), signal energy, contrast, brightness and exposure value.

Other aspects of the invention include methods corresponding to the devices and systems described above, and applications for the foregoing.

BRIEF DESCRIPTION OF THE DRAWINGS

The invention has other advantages and features which will be more readily apparent from the following detailed description of the invention and the appended claims, when taken in conjunction with the accompanying drawings, in which:

The figures depict embodiments of the present invention for purposes of illustration only. One skilled in the art will readily recognize from the following discussion that alternative embodiments of the structures and methods illustrated herein may be employed without departing from the principles of the invention described herein.

DETAILED DESCRIPTION OF THE PREFERRED EMBODIMENTS

Figure 1A:
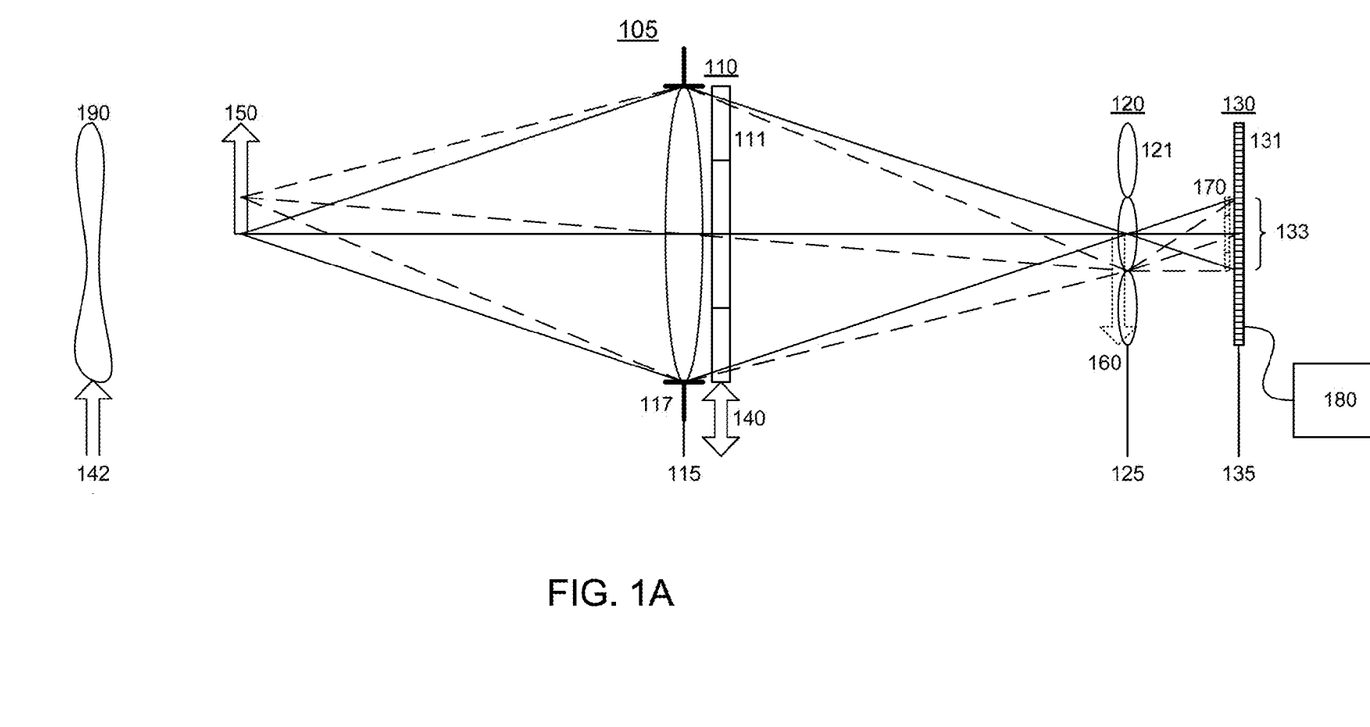
FIG. 1A is a diagram of an adjustable multimode lightfield imaging system according to the invention.
Figure 1B:
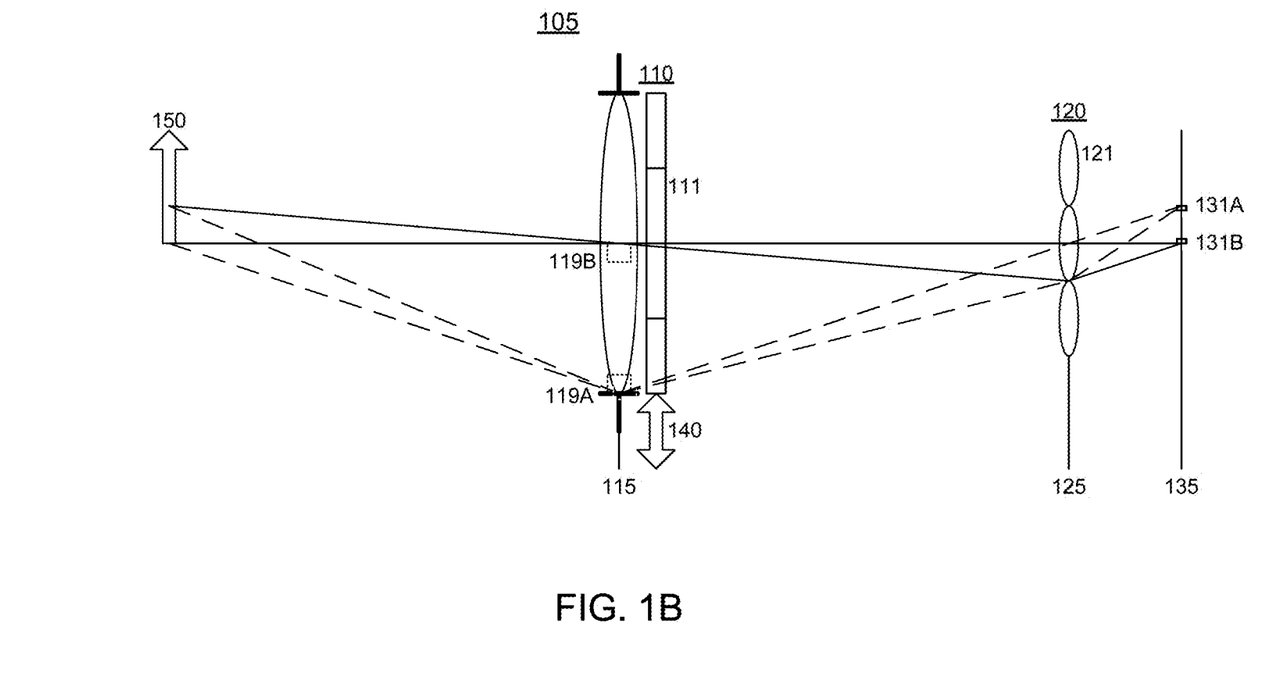
FIG. 1B illustrates the projection of a detector onto the pupil plane.
Figure 1C:
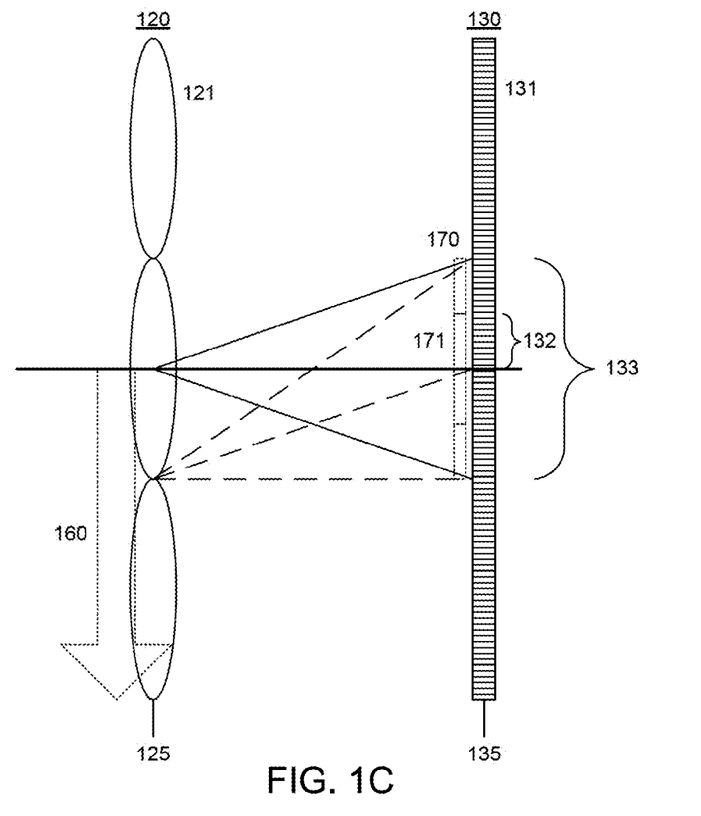
FIG. 1C is a detail of FIG. 1A.

FIGS. 1A-1C are diagrams of an adjustable multimode lightfield imaging system according to the invention. The system captures a multimode image of an object 150. The object 150 may be illuminated by a separate source 190, such as would be the case in a microscope setting. The multimode lightfield imaging system includes an image-forming optical module 105, which in FIG. 1 is represented by a single lens element although it is understood that the optical module 105 could contain multiple elements and/or non-lens elements (e.g., mirrors). The optical module 105 forms an optical image 160 of object 150. The optical image 160 is formed at an image plane 125 of the optical module 105. The optical module 105 is characterized by a pupil 117 and pupil plane 115, which in FIG. 1 is represented by a physical stop co-located with the single lens element. In more complex optical modules 105, the pupil 117 and pupil plane 115 need not be co-located with any of the optical elements within the optical module.

In a conventional imaging system, a detector array would be located at image plane 125 to capture the optical image 160. In a conventional color imaging system, an array of micro-filters (e.g., arranged in an R-G-B Bayer pattern) would be attached to the detector array at the image plane 125, so that each individual detector would capture red, green or blue channels of data.

However, this is not the case in FIG. 1. First, a non-homogeneous filter module 110 is positioned at the pupil plane 115. The filter module is non-homogeneous in that its filtering characteristics change as a function of location. In the following example, the filter module 110 is a filter array that includes different filters 111. For example, the filters 111 may have different wavelength responses, different polarization responses, or different luminance responses. However, the filter module is not required to be a filter array. It could be a filter with a continuously varying response, for example. A filter array is used in this example for purposes of illustration. Typically, the filter module will be larger than the pupil 117 so that only a portion of the filter module will be illuminated.

Second, an array 120 of micro-imaging elements 121 is located at the image plane 125. In FIG. 1, the micro-imaging elements 121 are shown as microlenses. Other elements can also be used, for example, an array of pinholes. The detector array 130 is located behind (i.e., optically downstream of) the array 120 of micro-imaging elements. More specifically, the detector array 130 is positioned in a conjugate plane 135 to the pupil plane 115. That is, each micro-imaging element 121 directs light from the pupil plane 115 to the detector array 130 in the conjugate plane 135.

In the case of microlenses, each microlens 121 forms an image 170 of the pupil (and filter module) at the conjugate plane 135. The corresponding section of the detector array 130 may contain a single detector 131 or multiple detectors 131 (preferably, multiple detectors), and will be referred to as a "subarray" 133. Thus, in the example of FIG. 1, the detector array 130 is subdivided into subarrays 133, and each microlens 121 images the pupil and filter module onto a corresponding subarray 133. Each subarray 133 contains one or more detectors 131.

Conversely, referring to FIG. 1B, each individual detector 131 can be projected through a microlens 121 to a corresponding location 119 in the pupil plane 115 and on the filter module 110. For that specific detector 131, the microlens 121 collects light from the corresponding location 119. FIG. 1B shows the projection of detector 131A through the center microlens to location 119A, and the projection of detector 131B to location 119B. The projection 119 of the detector preferably is magnified by at least 10× relative to the actual detector size 131.

Referring to FIG. 1C for more detail, each microlens 121 images the entire filter array 110 (that falls within the pupil) onto a subarray 133. Each filter 111 covers only a portion of the filter array 110, so the image 171 of each filter 111 will cover only a portion of the subarray 133. That portion will be referred to as a subpixel 132, as shown in the detail of FIG. 1C. That is, each microlens 121 directs light from a filter 111 to a corresponding subpixel 132. Each subpixel 132 may contain one or more detectors.

Each detector 131 collects the light from one filter 111 that travels through one microlens 121. The microlens array 120 is located in a conjugate plane to the object 150, so there is also an imaging relationship between the object 150 and the microlens array 120. Therefore, the light incident on a microlens is light originating from a portion of the object, not from the entire object. Thus, each detector 131 collects the light from a corresponding portion of the object (as determined by the extent of the microlens), as filtered by a corresponding filter 111.

Figure 2A:
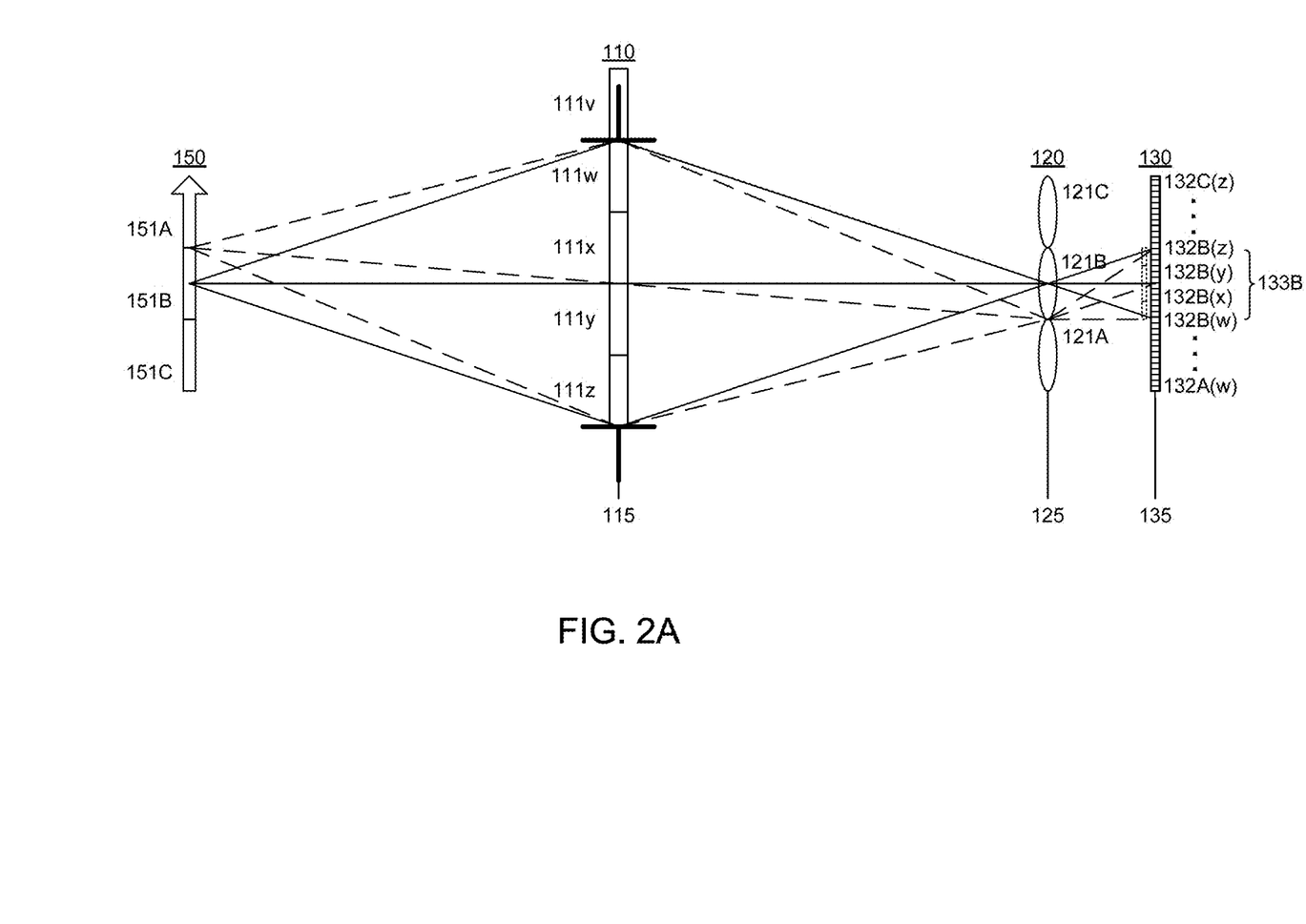
FIGS. 2A and 2B are diagrams further illustrating the operation of the system of FIG. 1.

FIG. 2A illustrates this concept in more detail. For clarity, the main lens 105 is omitted. In this example, the object 150 is divided into three subobjects 151A,B,C. Similarly, the illuminated portion of the filter array 110 includes four filters 111w,x,y,z. The filter module 110 is larger, also containing filter 111v which is not illuminated in FIG. 2A. The object 150 is imaged onto the microlens array 120. More specifically, the subobject 151B is imaged onto microlens 121B. This means that every ray that leaves subobject 151B will travel through the pupil (and through different filters 111, depending on where in the pupil) and arrive at microlens 121B. Similarly, subobject 151A is imaged onto microlens 121A, and subobject 151C is imaged onto microlens 121C.

Analogously, microlens 121B will image the entire filter array 110 (at least the illuminated portion) onto subarray 133B. Thus, filter 111w will be imaged by microlens 121B onto subpixel 132B(w), filter 111x onto subpixel 132B(x), and so on for the other filter/subpixel pairs, and for the other microlenses 121. For detectors 131 that fall entirely within subpixel 132B(w), those detectors will detect the light coming from subobject 151B passing through filter 111w. The same is true for the other subpixels 132A(w)-132C(z).

The imaging system is a "lightfield" imaging system because the rays collected by a detector are a function of not only the position in the object plane (as is the case in conventional imaging systems), but also a function of the position in the pupil plane. The imaging system is a multimode imaging system because the filter module 110 captures multimode information. These systems are sometimes referred to as plenoptic imaging systems.

Referring again to FIG. 1, a digital processing unit 180 collects the data from the detector array 130 and processes it accordingly. As a simple example, the digital processing unit 180 may reorder the data, collecting together the data from subpixels 132A(w), 132B(w) and 132C(w) in order to form an image as filtered by filter 111w. The same can be done for filters 111x,y,z.

Figure 2B:
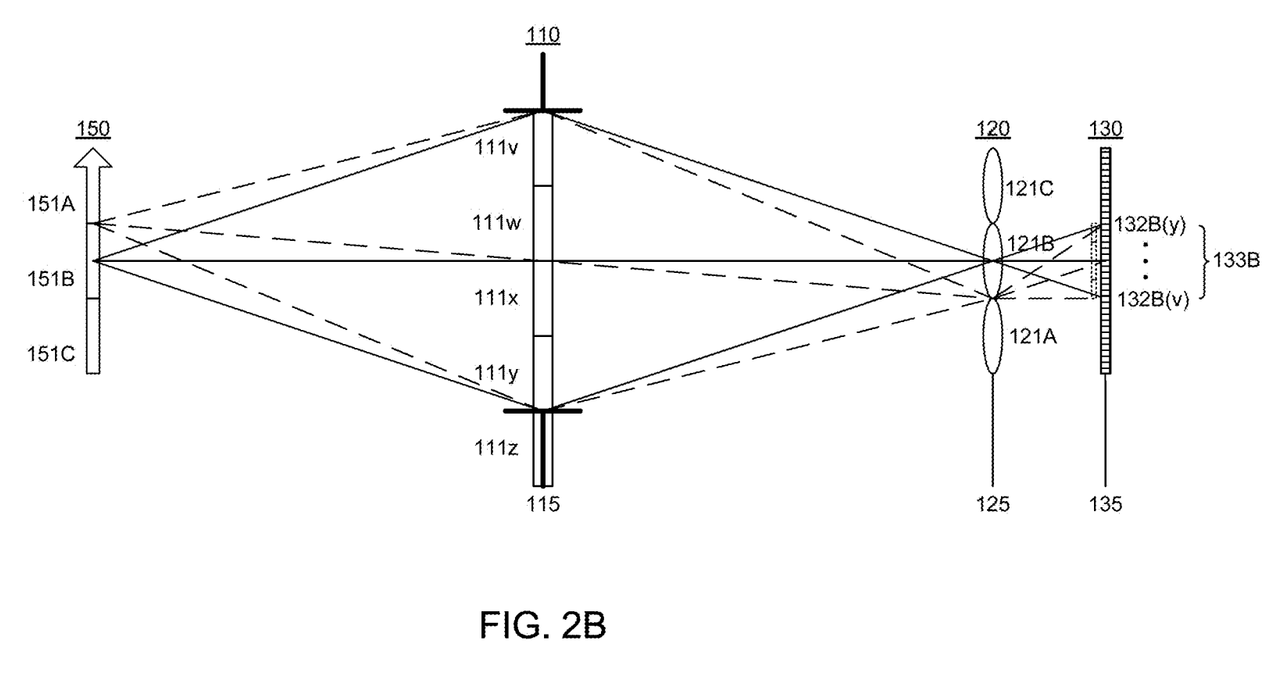

The system also includes an actuator 140 and a source controller 142. The actuator 140 can change the position of the filter module 110 relative to the optical module 105. In this way, which filters 111 are directed to which subpixels 132 can be changed, thereby changing the effective filtering. For example, in FIG. 2B, the filter array 110 has been translated downward so that filters 111v,w,x,y are now illuminated. The source controller 142 can change the strength of the source illumination 190 accordingly. For example, the new filter set may benefit from stronger or weaker illumination. FIG. 1A shows a controller 142 that adjusts source 190, but the controller can use other mechanisms to adjust the overall exposure. For example, the controller may adjust the attenuation of a neutral density filter located somewhere in the system to adjust the overall light throughput without changing the strength of the source illumination. Alternately, the controller may increase or decrease the exposure/integration time for the detectors 131. The term "exposure condition" will be used to refer to these quantities. The adjustment to the exposure condition may be made based on increasing SNR, signal energy, contrast, brightness, exposure value or other image quality metrics.

Figure 9A:
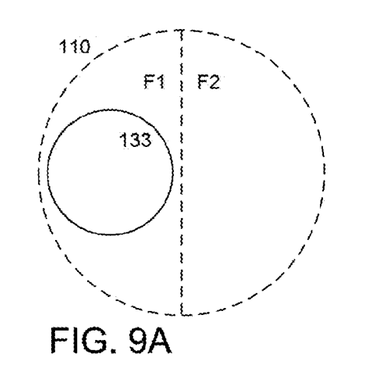
FIGS. 9A-9D show a two-filter filter module in different positions relative to the detector subarray.
Figure 9B:
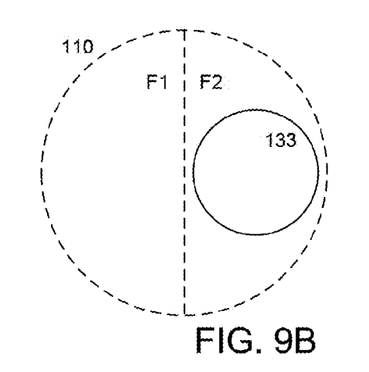
Figure 9C:
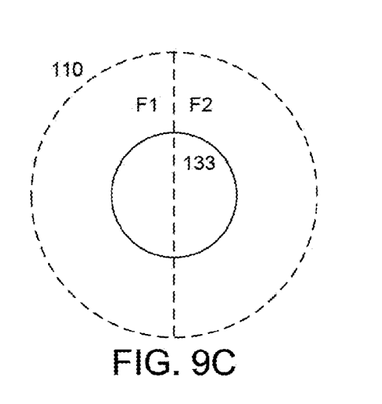
Figure 9D:
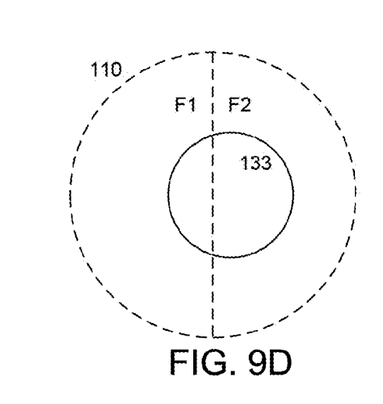
Figure 10A:
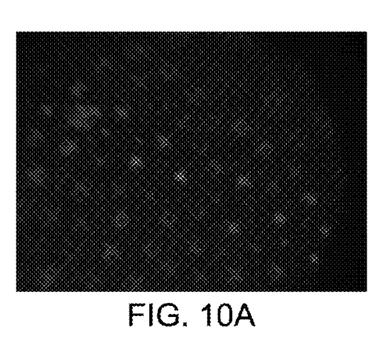
FIGS. 10A-10D are multimode images corresponding to the filter module positions of FIGS. 9A-9D, respectively.
Figure 10B:
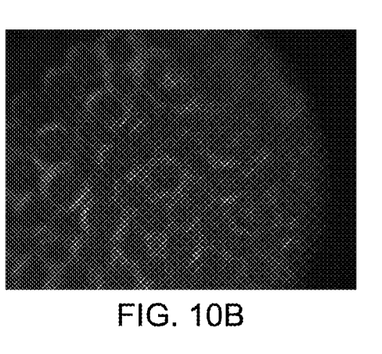
Figure 10C:
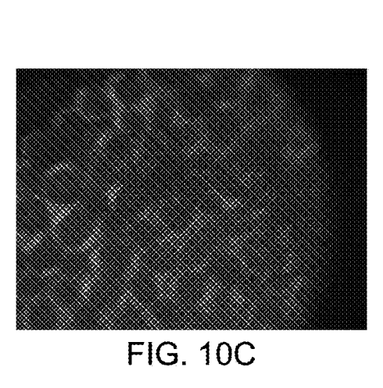
Figure 10D:
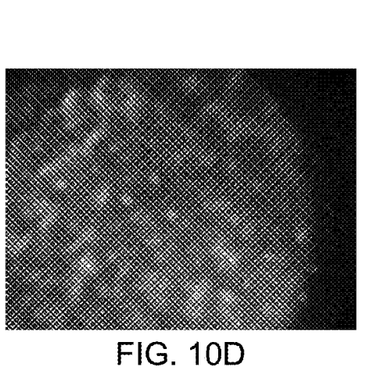
Figure 11:
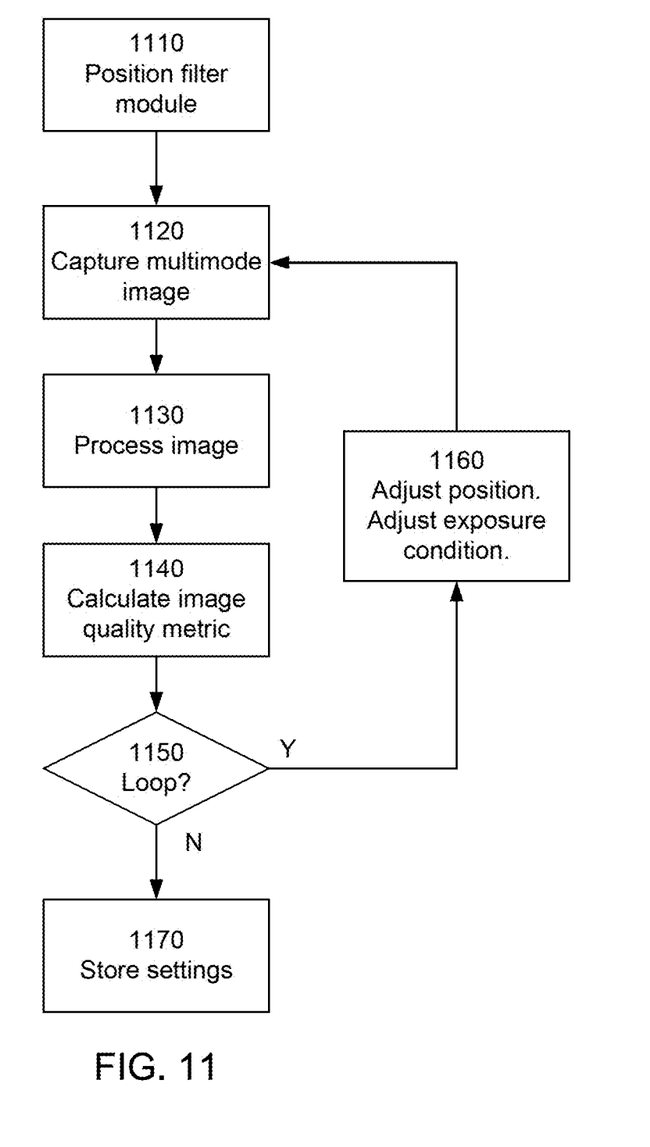
FIG. 11 is a flow diagram of an example method for adjusting filter module position and exposure condition.

FIGS. 3-8 show some examples of relative motion, and FIGS. 9-11 show some examples of adjustment of the exposure condition.

Figure 3:
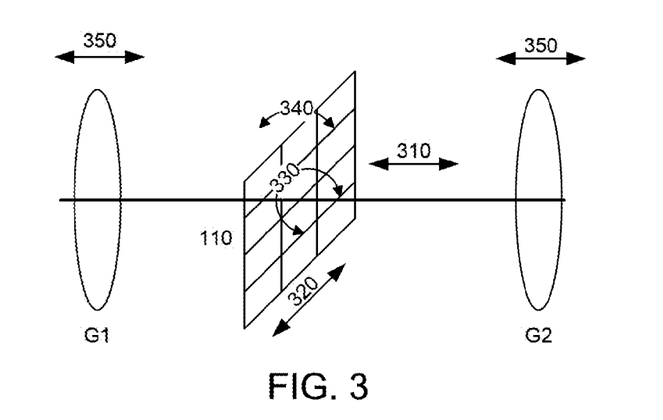
FIG. 3 is a diagram showing different types of relative movement between the filter module and the optical module.

FIG. 3 is a diagram showing different types of relative movement between the filter module 110 and the optical module. In this example, the optical module 105 contains two lens groups G1 and G2, with the pupil plane and filter module 110 located between the two lens groups. As one example, the actuator 140 might translate the filter module 110 relative to the optical module 105, along a direction 310 parallel to an optical axis, along a direction 320 that lies in the pupil plane, or along other directions. Alternately, the actuator 140 might rotate 330 the filter module 110 within the pupil plane. As another example, the actuator 140 might tilt 340 the filter module 110 relative to the optical module 105. Note that the actuator may move the optical module (or optical elements within the optical module) rather than moving the filter module, so long as there is relative motion between the filter module and the optical module. Movement 350 shows movement of optical elements within the optical module, for example a zoom action.

Figure 4A:
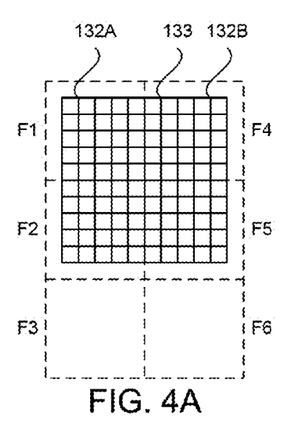
FIGS. 4A-4C show an example based on a filter array translated in the pupil plane.
Figure 4B:
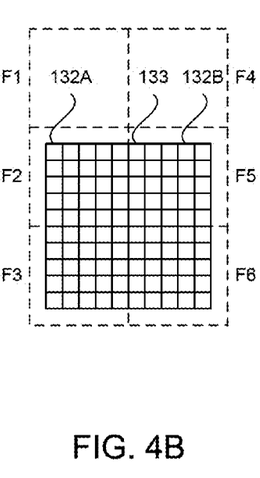
Figure 4C:
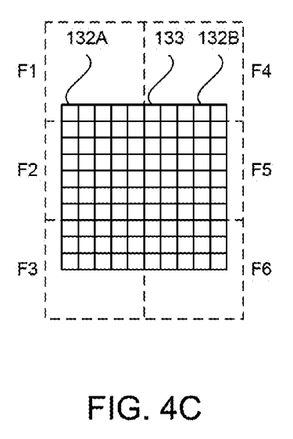

FIGS. 4A-4C show the illumination of a filter array 110, when it is translated along a direction that lies in the pupil plane. In this example, the filter array contains four filters F1-F6, as indicated by the dashed outlines. The projection of the detectors from one subarray 133 (i.e., the detectors corresponding to one microlens) are shown by the solid lines. For convenience, the subarray 133 is shown as square although typically it will be round since the pupil most often is round. Each square within detector subarray 133 represents a different detector 131.

Each of FIGS. 4A-C corresponds to the filter array in a different position. In the position of FIG. 4A, light illuminates the filter set F1,F2,F4,F5 of the array. The light passing through filter F1 is collected onto 25 detectors which form subpixel 132A corresponding to filter F1, and those signals correspond to light filtered by F1. Similarly, the 25 detectors forming subpixel 132B collect light passing through filter F4, and there are corresponding subpixels collecting light passing through filters F2 and F5. All of the light for each subpixel originates from the same subobject since it is all passing through the same microlens. Thus, each of the subpixels captures spectral (or other multimode) information about one subobject region of the overall object.

In FIG. 4B, the filter array has been moved. In this position, light illuminates the filter set F2,F3,F5,F6 of the array. The 25 detectors in subpixel 132A collect light passing through filter F2, the 25 detectors in subpixel 132B collect light passing through filter F5, and so on.

In many cases, the filter array may be positioned so that each filter covers an equal number of detectors. However, this is not required. In the position of FIG. 4C, light from filter F1 illuminates only 5 detectors in subpixel 131A, light from filter F2 illuminates 30 detectors, and light from filter F3 illuminates 15 detectors. FIG. 4 is just an example. The filter array may have alternate geometric layouts and shapes as well as different combinations of filters in order to implement various multimode imaging.

This architecture has several advantages over a conventional approach. A conventional approach might use two filter wheels, one containing filters F1,F2,F4,F5 when that spectral analysis is desired and another containing filters F2,F3,F5,F6 for the alternate spectral analysis. When the F1,F2,F4,F5 filter wheel is used, each of the filters F1,F2,F4,F5 rotates through the illumination path in sequence. This results in time multiplexing of the spectral information (rather than single snapshot capture of the spectral information). Furthermore, if the F2,F3,F5,F6 analysis is desired, the filter wheel must be changed, rather than simply shifting the filter module as in FIG. 4.

Figure 5A:
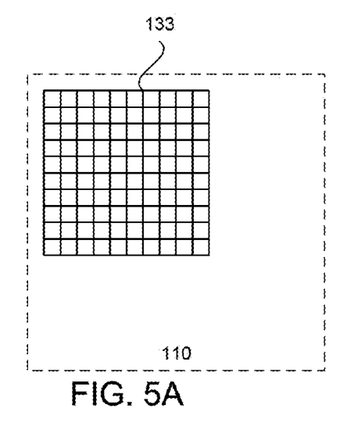
FIGS. 5A-5B show another example based on a non-arrayed filter module translated in the pupil plane.
Figure 5B:
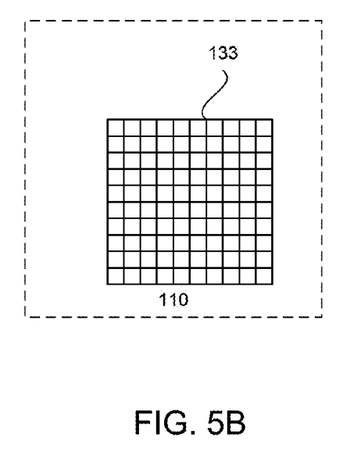

FIGS. 5A-5B show an example where the filter module is not an array, but is a continuously varying non-homogeneous filter. In this example, the filter module 110 varies in both x and y. For example, the filter module might be a wavelength filter that has a different center wavelength along the x direction and a different filter bandwidth along the y direction. When the filter module is moved from position 5A to 5B, each subarray will capture different information depending on which part of the filter module corresponds to that subarray.

As another example, the filter module in FIG. 5 might have a wavelength response that varies as a function of x and a polarization response that varies as a function of y. Furthermore, this might be implemented as two filters, a wavelength filter and a polarization filter, which are moved independently of each other.

Figure 6A:
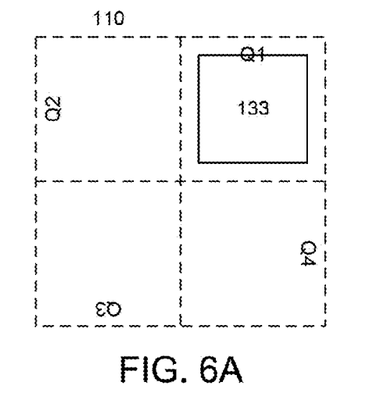
FIGS. 6A-6B show an example based on a filter array rotated in the pupil plane.
Figure 6B:
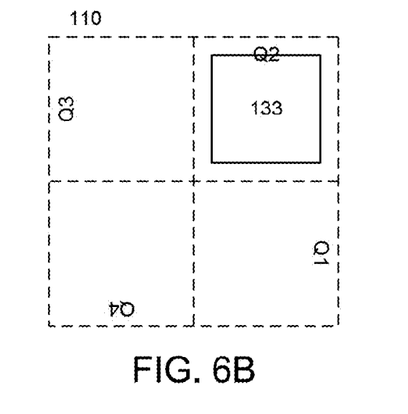

FIGS. 6A-6B show an example based on a filter module rotated in the pupil plane. In this example, the filter module has four quadrants Q1-Q4 that have different filter responses. Solid outline 133 is the outline of a subarray of detectors projected onto the pupil plane. In FIG. 6A, quadrant 1 is illuminated. In FIG. 6B, the filter module is rotated clockwise by ninety degrees and quadrant 2 is illuminated, resulting in a different filtering.

Figure 7A:
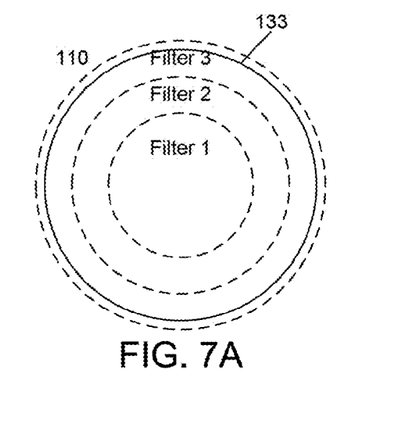
FIGS. 7A-7B show an example based on movement along the optical axis.
Figure 7B:
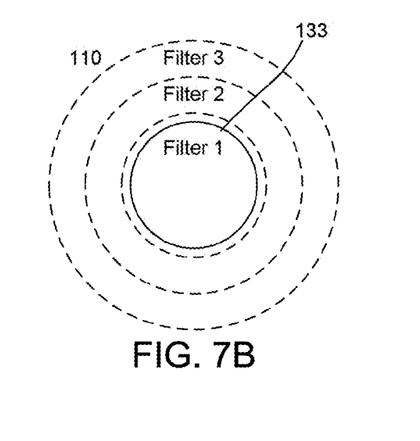

FIGS. 7A-7B show an example based on movement along the optical axis. In this example, the filter module is a set of concentric filters 1-3. In the position of FIG. 7A, all three filters are illuminated (as indicated by the solid circle 133). In FIG. 7B, only the center filter 1 is illuminated. This might be achieved with a zoom lens, for example. Referring to FIG. 3, both lens groups G1 and G2 might move along the optical axis. If the filter module is positioned between the two lens groups, then zooming the lenses can change the footprint of the optical beam on the filter module, with the consequence that light passes only through a larger or smaller portion of the filter module. If the filter module is segmented as in FIG. 7, in the zoom-in configuration only a few filters in the inner rings might be used effectively, whereas in the zoom-out configuration the filters of the outer rings might also be used.

This approach might be used in an application where spatial and spectral resolution are traded off. Detailed images of the object (i.e., high spatial resolution) may be formed when zoomed in, but with lower spectral resolution or less spectral information. When zoomed out, increased spectral resolution may be achieved at the expense of spatial resolution.

Other types of movement can also be used to change which filters are illuminated.

As a final example, consider a multispectral imaging task that involves detecting different types of spectral signals. For example, the classification of plant matter as either dry or fresh requires different spectral signatures for different crop types such as rice, corn, wheat. Preferably, a single, multispectral imaging system could be adjusted to address the different crop types, rather than requiring a separate filter wheel for each crop type.

Figure 8A:
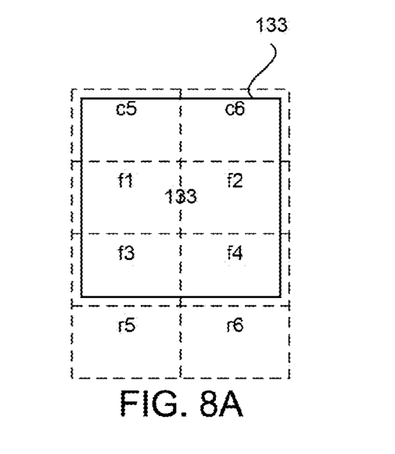
FIGS. 8A-8B show an example for distinguishing between dry and fresh vegetation, for both corn and rice.
Figure 8B:
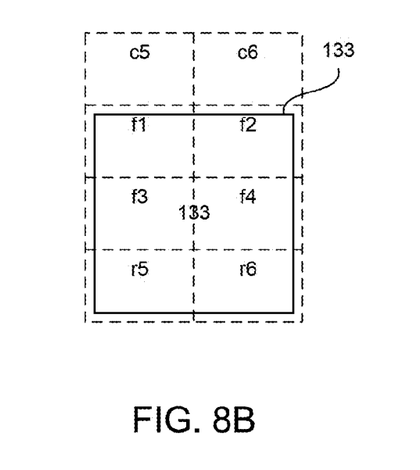

FIGS. 8A-8B show an example filter array for differentiating between dry and fresh vegetation using a simple shift of the filter module in the pupil plane. The filters f1-f4 and c5, c6, r5, r6 are specified in Tables 1-3.

TABLE 1

Filter specifications for common filters used to detect fresh/dry rice/corn leaf

| index | filter (Long/Short) | Cut off (nm) | transmittance (%) |
|---|---|---|---|
| f1 | L | 450 | 0.55 |
| f2 | L | 500 | 0.55 |
| f3 | L | 550 | 0.55 |
| f4 | S | 950 | 0.55 |

TABLE 2

Filters specifications for corn-specific filters

| index | center wavelength (nm) | bandwidth (nm) | transmittance (%) |
|---|---|---|---|
| c5 | 900 | 70 | 0.6 |
| c6 | 950 | 40 | 0.45 |

TABLE 3

Filter specifications for rice-specific filters

| index | center wavelength (nm) | bandwidth (nm) | transmittance (%) |
|---|---|---|---|
| r5 | 600 | 80 | 0.6 |
| r6 | 650 | 70 | 0.6 |

Filters f1-f4 and c5,c6 are used to identify corn, and to distinguish between fresh and dry corn leaf. Filters f1-f4 and r5,r6 are used to identify rice, and to distinguish between fresh and dry rice leaf. Note that filters f1-f4 are shared filters that are common to both corn and rice. The filter specifications in Tables 1-3 were chosen from a dictionary of commercially available filters.

When detecting corn, the filter array is positioned as shown in FIG. 8A relative to the subarray 133, thus illuminating filters f1-f4 and c5,c6. When detecting rice, the filter array is positioned as shown in FIG. 8B, using filters f1-f4 and r5,r6. Thus a single system can be used for both corn and rice.

The use of a non-homogeneous filter module allows the capture of a multimode image in a single snapshot. That is, images filtered by filters F1, F2, etc. can be acquired simultaneously. However, different modes may benefit from different illuminations. For example, if F1 is a red filter and F2 is a blue filter and the detector array or scene is more sensitive to red than to blue, then the blue image may benefit from a stronger illumination. However, since both the red and blue images are acquired simultaneously, stronger illumination will produce stronger illumination for both the red and blue images. This can be addressed by both repositioning 140 the filter module and adjusting 142 the source strength (or other exposure condition).

FIGS. 9-10 illustrate this concept. In this example, the filter module 110 has two bandpass wavelength filters. Filter F1 is centered at 450 nm and filter F2 is centered at 650 nm. FIG. 9A shows the subarray 133 when only filter F1 is used. The corresponding image of a petal is shown in FIG. 10A. Note that there are spots on the surface. FIG. 9B shows the subarray 133 when only filter F2 is used. The corresponding image of a petal is shown in FIG. 10B. Note that there are rings on the petal surface. FIG. 9C shows the subarray 133 when both filters F1 and F2 are used, but they are used in equal proportion. That is, filter F1 occupies 50% of the pupil and filter F2 occupies the other 50%. The resulting multimode image is shown in FIG. 10C. Note that the rings at 650 nm are visible but the spots at 450 nm are not. This is because the 450 nm component requires longer exposure or stronger illumination. However, just increasing the exposure could overexpose the 650 nm component.

FIGS. 9D and 10D show a solution. The filter module is positioned so that the 450 nm filter F2 occupies more of the pupil area, as shown in FIG. 9D. The exposure condition is also adjusted so that components from both filters F1 and F2 receive the correct exposure. In this example, the sum of the photons collected at all detectors behind each filter is optimized. Care is taken to adjust the exposure/light power versus the filter area such that the detectors behind each filter is not saturated. The resulting multimode image is shown in FIG. 10D. Both the 450 nm spots and the 650 nm rings are visible.

FIG. 11 is a flow diagram of this solution. The filter module begins at some initial position 1110. For example, it may be positioned so that different filters cover the same pupil area. With the filter module in this position, a multimode image is captured 1120 and processed 1130. The processed image is used to calculate 1140 an image quality metric. Examples of image quality metric include SNR, signal energy, contrast, brightness and exposure value. If the quality is not sufficient 1150, then the position of the filter module and the exposure condition are adjusted 1160. This is repeated until sufficient quality is obtained. The resulting settings may be store 1170.

The multimode image can be processed 1130 in many ways, which may affect the image quality metric 1140. For example, the processed image could be produced by summing or averaging all the detectors corresponding to each filter. Alternately, several sub-images for one filter could be produced by demultiplexing the detectors behind a lenslet into one sub-image. If the second method is chosen, then further processing might be applied to better define the image quality metric. This additional processing could be averaging all the sub-images for a given filter, or choosing features that are best in each sub-image to define a "sharpest feature" image, a "highest SNR" image, etc.

The following is another example method for determining the exposure condition corresponding to the position for the filter module. Let Q be the image quality metric. Assume there are K filters $f_k$. In this example, there is an initial calibration (steps 1 and 2) before taking a sequence of images.

Step 1. For different positions for the filter module, determine which detectors fall within which subpixel corresponding to each filter $f_k$, k=1, . . . K. That is, for filter module position 1, which detectors will collected light filter by filter $f_1$, which will collected light filtered by $f_2$, etc. This can be done experimentally or through modeling or simulation. For example, geometric optics calculations can be used to propagate light passing through a filter onto the detector array.

Step 2. Position the filter module such that only one of the filters $f_k$ is exposed (e.g., as shown in FIG. 9A or 9B). Determine the optimal exposure condition, for example the strength level $L_{k,cal}$ for the source and the integration/exposure time $T_{k,cal}$. Compute the corresponding image quality metric $Q_{k,cal}$. Repeat this for each filter. At this point, there will be K image quality metrics $Q_{k,cal}$, one for each filter.

Step 3. Position the filter module such that each filter $f_k$ covers an equal area of the pupil (e.g., as shown in FIG. 9C). Adjust the exposure condition for single-snapshot acquisition. Let $L_0$ and $T_0$ be the illumination and exposure time. Compute the image quality metric $Q_{k,0}$ for each subimage. That is, compute the image quality metric for each set of detectors corresponding to one filter.

Step 4. Process other positions of the filter module as follows:
For the new position, identify which of the filters $f_k$ have increased in area and which have decreased. For example, in FIG. 9D, filter F2 has increased in area relative to FIG. 9C, whereas filter F1 has decreased in area. Let $\{f_{k\_m}, m=1, \ldots M\}$ be the set of filters that has increased in area and let $\{f_{k\_n}, n=1, \ldots N\}$ be the set of filters that has decreased in area.
Compute $Q_{k\_n,new}$ for the subimages where the filter has decreased in area. These are the subimages that are most likely to suffer reduced image quality because the total light throughput for those subimages has decreased due to the decreased pupil area.
Adjust the exposure condition such that the image quality metrics $Q_{k\_n, new}$ for the decreased area filters are satisfactory. The following are some possible ways to do so:
Increase the illumination and/or exposure time until the computed image quality metric $Q_{k\_n,new}$ reaches the calibration value, e.g.

$$\max_{k\_n}(Q_{k\_n,new}) = \min_{k\_n}(Q_{k\_n,cal}), \text{ or}$$

$$\max_{k\_n}(Q_{k\_n,new}) = \text{mean}_{k\_n}(Q_{k\_n,cal}).$$

Increase the illumination and/or exposure time until detectors illuminated by filters $f_{k\_n}$ are saturated.
Set the illumination to halfway between the current illumination setting and the average of the $L_{k\_n,cal}$:

$$L_{new} = [L_{old} + \text{mean}_{k\_n}(L_{k\_n,cal})]/2.$$

Adjust the exposure condition according to specifications of quality metric $Q_{k\_n,new}$ in configuration file (e.g., via pre-created look-up-tables).
In some cases, increasing the illumination and/or exposure time may result in saturation, so that can also be checked for.
Check that the exposure condition for $Q_{k\_m,new}$ (i.e., for the increased area filters) are also satisfactory. For example, the steps above may result in increased illumination and/or exposure. Too much increase may saturate the subimages for the filters which have increased in area.

In a special case, the image quality metric is the exposure value $$EV = \log_2(A/T) \tag{1}$$

where A is the area of the pupil covered by the relevant filter and T is the integration/exposure time. In this case, some of the calculations are simplified due to the log nature of the exposure value. In another variation, the approach described above can be used but without the initial calibration phase.

As different exposure conditions are determined for different positions of the filter module, this information can be stored for future use. In one approach, the data is stored in a lookup table. Then, as different filter module positions are used in the field, the corresponding exposure conditions can be determined from the lookup table.

Although the detailed description contains many specifics, these should not be construed as limiting the scope of the invention but merely as illustrating different examples and aspects of the invention. It should be appreciated that the scope of the invention includes other embodiments not discussed in detail above.

For example, many types of filter arrays can be implemented. Filters can have different wavelength responses. All of the filters can be different, or some can be different and some the same. Multiple filters or filter arrays can also be used. For example, multiple filter arrays or filter modules can be used, each of which is moved independently of the others (or not). The number and type of wavelength responses can also vary, depending on the application. Some applications will use many different wavelength filters: 10, 20, 25 or more. In some cases, specific wavelength lines are being detected, so narrow band interference filters may be used. Filters other than wavelength filters can also be used, for example polarization, luminance, and neutral density filters.

Filtering can also be implemented at other points in the system. For example, the invention does not prevent the use of traditional micro-filters with the detector array. Various types of optical modules can also be used, including reflective and catadioptric systems. In some applications, the optical module is preferably telecentric. Finally, terms such as "light" and "optical" are not meant to be limited to the visible or purely optical regions of the electromagnetic spectrum, but are meant to also include regions such as the ultraviolet and infrared (but not be limited to these).

Various other modifications, changes and variations which will be apparent to those skilled in the art may be made in the arrangement, operation and details of the method and apparatus of the present invention disclosed herein without departing from the spirit and scope of the invention as defined in the appended claims. Therefore, the scope of the invention should be determined by the appended claims and their legal equivalents.

What is claimed is:

1. An adjustable multimode lightfield imaging system comprising:
   an optical module that forms an optical image of an object, the optical module characterized by imaging optics, a pupil located at a pupil plane and an image plane;
   a filter array positioned approximately at the pupil plane, the filter array including a plurality of different filters, the filter array moveable relative to the optical module wherein for different positions of the filter array, the filters in the filter array occupy different fractions of the pupil;
   an array of micro-imaging elements positioned approximately at the image plane;
   a detector array positioned such that the micro-imaging elements image the filter array onto the detector array, the detector array capturing a multimode image of the object according to an exposure condition and a position of the filter array, the multimode image comprising images of the object filtered by different filters in the filter array; and
   a controller that adjusts both the exposure condition and the position of the filter array in conjunction with one another.

2. The lightfield imaging system of claim 1 wherein the filter array is moveable along a direction that lies in the pupil plane.

3. The lightfield imaging system of claim 2 wherein the controller adjusts the exposure condition in response to positions of the filter array where, at different positions of the filter array, the same filters in the filter array occupy the pupil but the filters occupy different fractions of the pupil.

4. The lightfield imaging system of claim 1 wherein the controller adjusts a strength of a source illuminating the object.

5. The lightfield imaging system of claim 1 wherein the controller adjusts light throughput of the optical module.

6. The lightfield imaging system of claim 1 wherein the controller adjusts attenuation of a neutral density filter.

7. The lightfield imaging system of claim 1 wherein the controller adjusts exposure/integration time of the detector array.

8. The lightfield imaging system of claim 1 wherein the controller adjusts the exposure condition in response to an image quality metric of the multimode image.

9. The lightfield imaging system of claim 8 wherein the image quality metric is a signal to noise ratio.

10. The lightfield imaging system of claim 8 wherein the image quality metric is a signal energy.

11. The lightfield imaging system of claim 8 wherein the image quality metric is an exposure value.

12. The lightfield imaging system of claim 1 wherein the controller accesses a lookup table to determine the adjustment to the exposure condition.

13. The lightfield imaging system of claim 1 wherein the filter array includes filters with different wavelength responses.

14. The lightfield imaging system of claim 1 wherein the filter array implements multispectral imaging.

15. The lightfield imaging system of claim 1 wherein the array of micro-imaging elements includes a microlens array.

16. The lightfield imaging system of claim 1 wherein the optical module is telecentric.

17. The lightfield imaging system of claim 1 wherein the pupil plane has a magnification of at least 10:1 relative to the detector array.

18. A method for adjusting a plenoptic imaging system having a filter array positioned approximately at a pupil plane of the plenoptic imaging system, the filter array including a plurality of different filters, the filter array moveable relative to the pupil plane wherein for different positions of the filter array, the filters in the filter array occupy different fractions of the pupil, the method comprising:
   adjusting both an exposure condition for the plenoptic imaging system and the position of the filter array in conjunction with one another; and
   capturing, under the exposure condition, a multimode image of an object, the multimode image comprising images of an object filtered by different filters in the filter array, said filtering based on the position of the filter array.

19. The method of claim 18 wherein, at different positions of the filter array, the same filters in the filter array occupy the pupil but the filters occupy different fractions of the pupil.

20. The method of claim 18 wherein the step of adjusting the exposure conditions comprises adjusting a strength of a source illuminating the object.

* * * * *